United States Patent [19]
Friedrich et al.

[11] 4,055,496
[45] Oct. 25, 1977

[54] DIALYSIS APPARATUS

[75] Inventors: Richard A. Friedrich, Brighton; Robert L. MacNeill, Newburyport, both of Mass.

[73] Assignee: National Medical Care, Inc., Boston, Mass.

[21] Appl. No.: 550,169

[22] Filed: Feb. 18, 1975

Related U.S. Application Data

[63] Continuation of Ser. No. 462,411, April 19, 1974, abandoned.

[51] Int. Cl.² ............................................. B01D 31/00
[52] U.S. Cl. ..................................... 210/87; 210/94; 210/195 R; 210/321 B
[58] Field of Search ................. 210/22, 321 B, 195 R, 210/87, 94

[56] References Cited

U.S. PATENT DOCUMENTS

| | | | |
|---|---|---|---|
| 3,484,369 | 12/1969 | De Dobbeleer | 210/22 |
| 3,527,700 | 9/1970 | Goldhaber | 210/321 B X |
| 3,669,880 | 6/1972 | Marantz et al. | 210/22 |
| 3,722,680 | 3/1973 | Smith | 210/195 R X |
| 3,741,395 | 6/1973 | Zimmerman | 210/321 B |
| 3,743,098 | 7/1973 | Martinez | 210/321 B |
| 3,880,759 | 4/1975 | Van Assendelft | 210/321 B X |

*Primary Examiner*—Frank A. Spear, Jr.
*Attorney, Agent, or Firm*—Wolf, Greenfield & Sacks

[57] ABSTRACT

A dialysis module for use with a variety of single pass or single pass-recirculating artificial kidney dialyzers as desired. The apparatus has quick disconnects to allow attachment of a single pass kidney dialyzer or shunt tube so that a single housing can be used to provide two entirely different modes of operation as selected. A clear canister forms a part of the dialysis flow path in both modes of operation to enable rapid detection of blood leaks in either mode of operation.

15 Claims, 3 Drawing Figures

DIALYSIS APPARATUS

This is a continuation of application Ser. No. 462,411, filed Apr. 19, 1976 now abandoned.

BACKGROUND OF THE INVENTION

Dialysis has come into widespread use as a mode of treatment for persons having kidney failure. As is known, blood from a patient is passed through a dialyzer and the blood cleansed of harmful ingredients by dialysis through a membrane about which is established a flow of conventional dialysate fluids. The apparatus for mounting conventional artificial kidneys or dialyzers and providing dialysate flow about one side of a dialysis membrane, is normally specifically constructed with a view toward the particular type of dialyzer to be used. This creates a problem when only a single apparatus is available and treatment necessary requires the use of a dialyzer different from that which the specific apparatus is capable of handling.

The most common artificial kidney dialyzers are of one of two basic types. A first type is known as the single pass-recirculating dialyzer. Coil kidney dialyzers are often used in single pass-recirculating mode or systems such as the Ultraflow II dialyzer produced by Travenol Laboratories, Inc. of Morton Grove, Ill. Such dialyzers require high dialysate flow rates through the system, as for example, in excess of 15 liters per minute with the major portion being recirculating flow and another portion being original flow of fresh dialysate. No control over pressure of the dialysate is necessary in such apparatus and the dialyzer is open to atmospheric pressure.

In a second type of artificial kidney dialyzer, capillary or parallel flow membranes are provided. In such dialyzers, known as single pass dialyzers, the dialysate flows directly through parallel paths in a single pass about the membranes with no recirculation of the dialysate. Flow rates of from 100 cc to 1 liter per minute are often used. Such systems are closed to the atmosphere and pressure control of the dialysate in the dialyzer is used to provide desired pressure.

In the single pass type of artificial kidney dialyzers, conventional equipment does not normally provide for visual checking to determine whether or not blood has passed through the dialysis membrane and often, complicated blood leakage detecting devices are used for this purpose. It is important to detect blood leakage to prevent contamination of the system and loss of blood to the patient.

Although it is desirable to have a single dialysis apparatus which could accommodate all types of artificial kidney dialyzers and particularly all commonly commercially used types, no such single apparatus is generally available for use.

SUMMARY OF THE INVENTION

It is an important object of this invention to provide a dialysis apparatus for use with a variety of artificial kidney dialyzers including single pass or single pass-recirculating dialyzers.

Still another object of this invention is to provide a dialysis apparatus in accordance with the preceding object which enables ease of selection for use with single pass dialyzers or single pass-recirculating dialyzers.

Still another object of this invention is to provide a dialysis apparatus in accordance with the preceding objects which apparatus permits visual detection of blood leak loss in dialysis operations.

Still another object of this invention is to provide a dialysis apparatus in accordance with the preceding objects which is highly efficient and safe for use over long operating life spans in conventional dialysis procedures.

According to the invention, a dialysis apparatus is provided for selective use with single pass or single pass-recirculating artificial kidney dialyzers. A single housing mounts a two mode system for use with either type of dialyzer. A dialysate canister is open to the atmosphere and carries a dialysate overflow pipe for limiting a level of dialysate in the canister. A dialysate flow conduit has a first inlet for connection to a source of a fresh dialysate fluid and an outlet opening to the canister. A mounting opening is provided in the canister for mechanically mounting an artificial kidney dialyzer therein. A recirculating pump means has a conduit interconnecting one portion of the canister with the mounting opening for permitting dialysate recirculation therethrough. A first shunt dialysis conduit is connected to the flow conduit at a first point intermediate the canister opening and the first inlet. The shunt dialysis conduit terminates at a first shunt connector. A second shunt connector is spaced from the first shunt connector. A second shunt dialysis conduit leads from the second shunt connector to a second point in the dialysate flow conduit preferably intermediate the outlet opening to the canister and the first point. The second shunt dialysate conduit preferably has first and second branches intermediate ends thereof with one branch carrying a negative pressure pump and the second branch carrying means for adjusting the value of negative pressure produced by the pump.

It is an important feature of the dialysis apparatus of this invention that it can be used with either a single pass or single pass-recirculating kidney dialyzer. A wide variety of conventional commercially available dialyzers can be interchangeably used with the apparatus of this invention using the dialysate system thereof interchangeably. Negative pressure can be obtained by the simple throwing of an electric switch. Dialysis can be rapidly started after testing of the dialyzer. Cold chemical disinfection can be carried out without the use of specialized adopters. Since the canister used is in the dialysate flow path in both single pass and single pass-recirculating modes of operation, visual inspection is possible to detect blood leak loss of at least as low as less than 5 cc in 6 hours time. Positive pressure relief is preferably provided by a valve which prevents the dialyzer from being subjected to dangerous levels of positive pressure. The apparatus can be constructed with substantially conventional components and provides high safety with good reliability in use.

BRIEF DESCRIPTION OF THE DRAWINGS

The above and other objects, advantages and features of the present invention will be better understood from the following specification when read in connection with the accompanying drawings in which.

DESCRIPTION OF PREFERRED EMBODIMENTS

Figure 1:
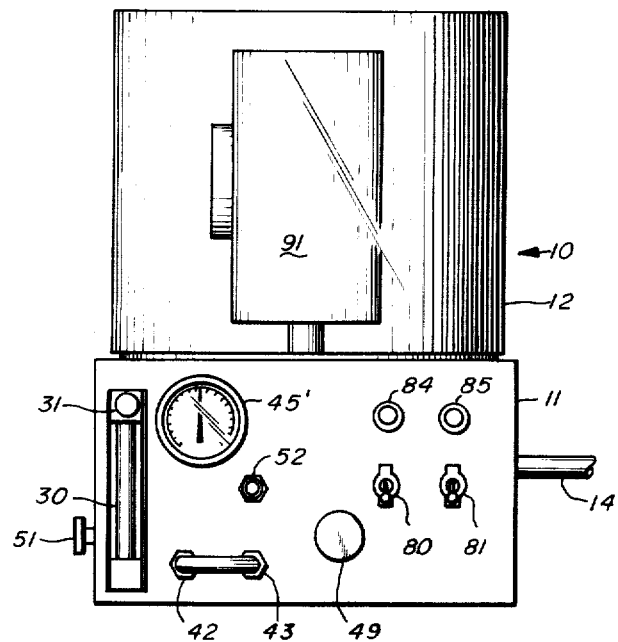
FIG. 1 is a front view of a preferred embodiment of a dialysis apparatus in accordance with this invention.

With reference now to the drawings and more particularly FIG. 1, a preferred embodiment of a dialysis module or apparatus is illustrated generally at 10. A housing 11 carries a top mounted dialysate canister 12 preferably formed of a clear, transparent plastic material such as polystyrene or polycarbonate and is open to the atmosphere. A dialysate quick disconnect 13 (FIG. 2) is mounted on the rear of the housing as is a quick disconnect (not shown) for a drain conduit 14.

The dialysis apparatus 10 is designed for use with a central station fresh dialysate delivery system of any conventional type. For example, a central system can be used which provides dialysate supplies to several modules, such as 10, to enable dialysate flow for carrying out blood dialysis on a plurality of patients at a plurality of stations.

The dialysate flow system is preferably formed of conventional plastic piping such as polyvinyl chloride tubing although stainless steel or other materials can be used. The dialysate flow system is carried substantially within the housing with the dialysate canister 12 preferably mounted at the top of the housing. The canister 12 is preferably cylindrical in form and has a bottom wall 15 resting on a top wall of the housing 11. An overflow pipe 16 extends up into the canister and is interconnected through the wall 15 to a drain outlet 14 as by conventional fittings (not shown). A dialysate flow conduit 20 is connected at one end to a self-sealing, quick disconnect 13 for connection with a source of fresh liquid dialysate as from a central dialysate supply as known in the art. An outlet opening 21 of the dialysate flow conduit 20 opens to the chamber 22 provided in the canister 12 through the bottom wall 15 of the canister. Opening 21 is preferably at the inlet of a recirculating pump 24 although it can pass directly into the canister. Thus the outlet opening 21 passes dialysate to the canister although the dialysate may first pass through the recirculating pump. A mounting opening 23 is also provided in the bottom wall 15 of the canister and enables plug in detachable mounting of conventional recirculating dialyzers directly in the chamber 22. The mounting opening has conventional rubber grommet means or other joint structure to enable ease of connecting and disconnecting the dialyzer when required. A recirculating pump 24 is provided in a conduit 25 which connects a portion 26 of the canister with the mounting opening 23 permitting dialysate recirculation from the chamber 22 and through a dialyzer mounted in the chamber 22.

A conventional flow meter 30 is positioned in conduit 20 for controlling flow of fresh dialysate. A flow meter such as a Model 10A3137M flow meter produced by Fisher and Porter Company of Warminster, Pa. can be used. A dialysate metering valve 31 which is preferably integral with the flow meter 30, regulates the rate of flow through conduit 20 of the fresh dialysate. Metering valve 31 is of a conventional type and is preferably hand adjustable although a fixed metering valve can be used if desired. A pressure relief check valve 32 is provided in the dialysate flow conduit 20 which prevents flow through conduit 20 toward the quick disconnect 13 in all modes of operation but allows a small flow in a direction away from the quick disconnect due to vacuum created in the upper portion of line 20 by the recirculating pump 24. The check valve of the preferred embodiment is a Model SS 4C-P2-1 produced by Nupro Company of Cleveland, Ohio although other check valves can be used. The check valve 32 acts as a safety valve in that if other pathways through the system are clogged as by kinked lines or backups, dialysate flow will pass through the check valve toward the canister at pressures above 1 psi enabling continuation of flow when single pass-recirculating dialyzers are used. However, it is preferred that when using single pass-recirculating dialyzers, flow be maintained through the other conduiting of the system as will be described to maintain all conduiting in a washed used condition and prevent contamination of the lines as might otherwise occur.

A first shunt dialysis conduit 40 is connected to the flow conduit 20 at a first point 41 intermediate the canister opening 21 and the quick disconnect 13. The conduit 40 leads to a self-sealing, quick disconnect or shunt connector 42 and carries a dialysate pressure gauge 45' to enable readout of dialysate pressure. The dialysate pressure gauge 45' can be mounted in other portions of the system if desired. Conventional pressure gauges such as Model 2 ½ 109 SXMS Ascroft produced by Dresser Industries, Inc. of Stratford, Conn. are suitable for use.

A second shunt connector in the form of a self-sealing quick disconnect 43 is preferably positioned on the front panel of the apparatus 10 and connected with a second shunt dialysis conduit 44 which leads to a second point 45 in the dialysate flow conduit 20 and has a first branch 46 and second branch 47. The first branch 46 has a negative pressure pump such as PQM dialysate negative pressure pump formed of Delrin with a 303 SS gear pump protected with lip seals produced by Greuler Company, Chicago Ill. A manually operable pressure regulating valve 49 is mounted in a branch pipe 47 which acts as a bypass of the negative pressure pump 48. The pressure regulating valve of the preferred embodiment is a Model 1RM4A valve produced by Whitey Co. of Oakland, Calif. The outlet at second point 45 can be located at the canister 12 rather than in line 20 or at other locations allowing filling of the canister for visual detection of blood leaks. When the valve 49 is closed, effluent dialysate passes through the negative pressure pump 48 solely and adjustment of the valve provides for varying degrees of negative pressure as for example from −500 to 0 mm of mercury. In the fully opened position of the valve, most dialysate passes through branch 47 when the pump is not in operation, but when the pump is operating there is a recirculating flow from branch 47 through the pump branch 46.

The recirculating conduit 25 is also connected with a conduit 50 having a manually operable drain valve 51 separating conduit 50 from the drain 14. A self-sealing quick disconnect 52 is provided on a flushing conduit 53 interconnected with conduit 50.

The quick disconnects 13, 42, 43 and 52 are of conventional design and allow plugging in of conduiting whereupon the path is opened and when the conduiting is unplugged, liquid leaks are prevented at fluid pressures normally encountered in the range of from 0 to 2 psi or higher. Quick disconnects such as Model No. 294PSS produced by Imperial Eastman Corp. of Chicago, Ill. can be used. Other connection means can be used in place of the quick disconnects. For example screw in couplings and manually operable turn valves can be used. The conduiting used in the preferred embodiment is preferably one fourth inch inside diameter conduiting throughout except for conduits 25, 50 and the drain outlet which are three fourths inch inside diameter conduits.

Figure 3:
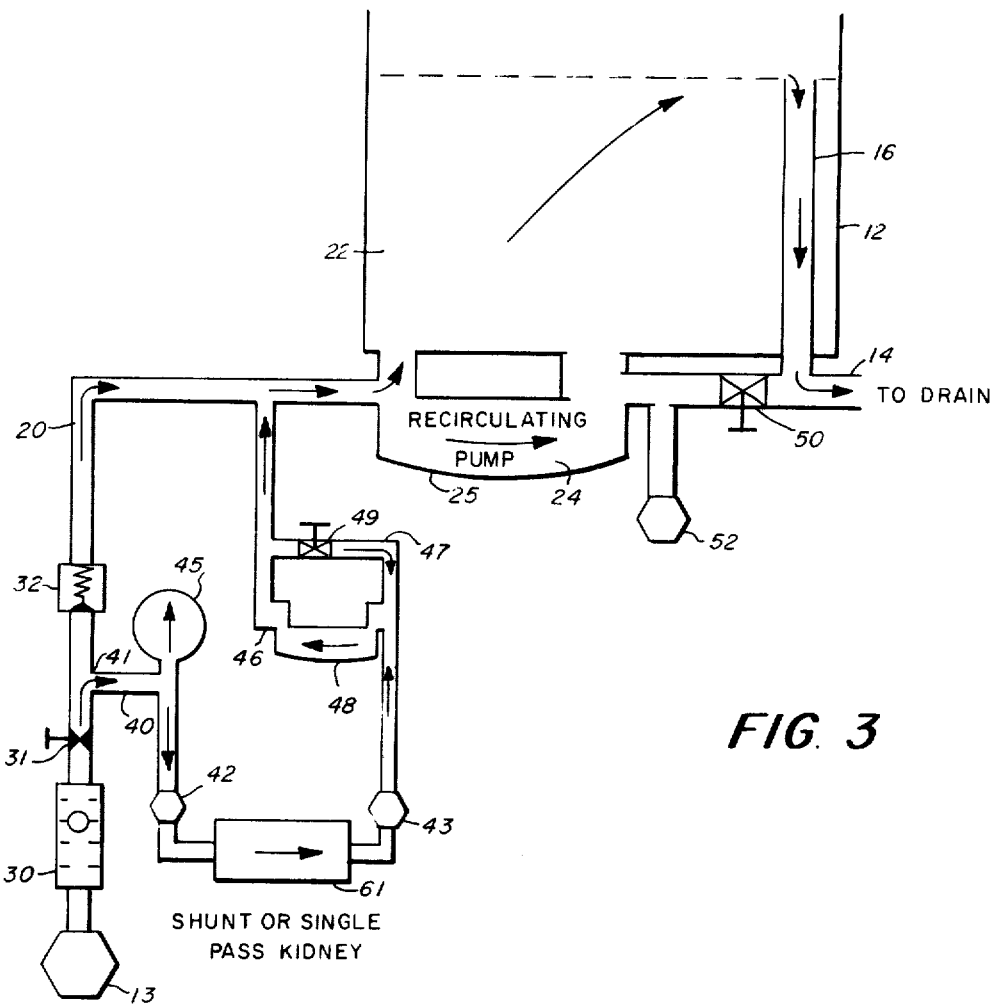
FIG. 3 is a semidiagrammatic drawing of the dialysate flow path system therein when used in a single pass mode of operation.

In the single pass mode of operation, the dialysate inlet of a single pass dialyzer 61, as shown in FIG. 3, is connected to quick disconnect 42 and the outlet connected to quick disconnect 43. Negative pressure pump 48 is turned on. No dialyzer is present in the canister 12. The blood flow path through the dialyzer is not shown in the drawings but is as conventional in the art with blood passed from and to the patient flowing within the membranes of the dialyzer. Fresh dialysate from the central delivery system is provided through quick disconnect 13 and flows through the flow meter 30. At the outlet of the flow meter it passes through the dialysate metering valve 31 which regulates the rate of flow. The dialysate is then conducted to the self-sealing quick disconnect 42 with dialysate pressure gauge 43 measuring dialysate pressure at this point in the system. The dialysate is then passed to the single pass kidney dialyzer diagrammatically shown at 61, to the inlet of the negative pressure pump 48 which is a positive displacement gear pump. The unrestricted flow of the negative pressure pump can be for example 1 liter per minute. With the dialysis flow restricted by closure of the dialysate metering valve 49 to 500 cc per minute, a high vacuum is produced in the dialysate fluid system bounded by the dialysate metering valve and the negative pressure pump. Degrees of negative pressure less than the maximum are produced by opening the dialysate pressure regulating valve 49 which provides dialysate recirculation back to the inlet of the pump thereby reducing vacuum or negative pressure. Effluent dialysate from the negative pressure pump passes into the recirculating system at the inlet 21 of the recirculating pump and fills the clear canister to the level at the top of the overflow tube 16 with the excess draining down the overflow tube into the drain. The recirculating pump is turned off in this mode of operation. The drain valve preferably remains closed during the course of treatment. Possible blood leaks from the artificial kidney can be detected by observation of turbidity of the effluent dialysate in the clear, transparent canister 12.

Figure 2:
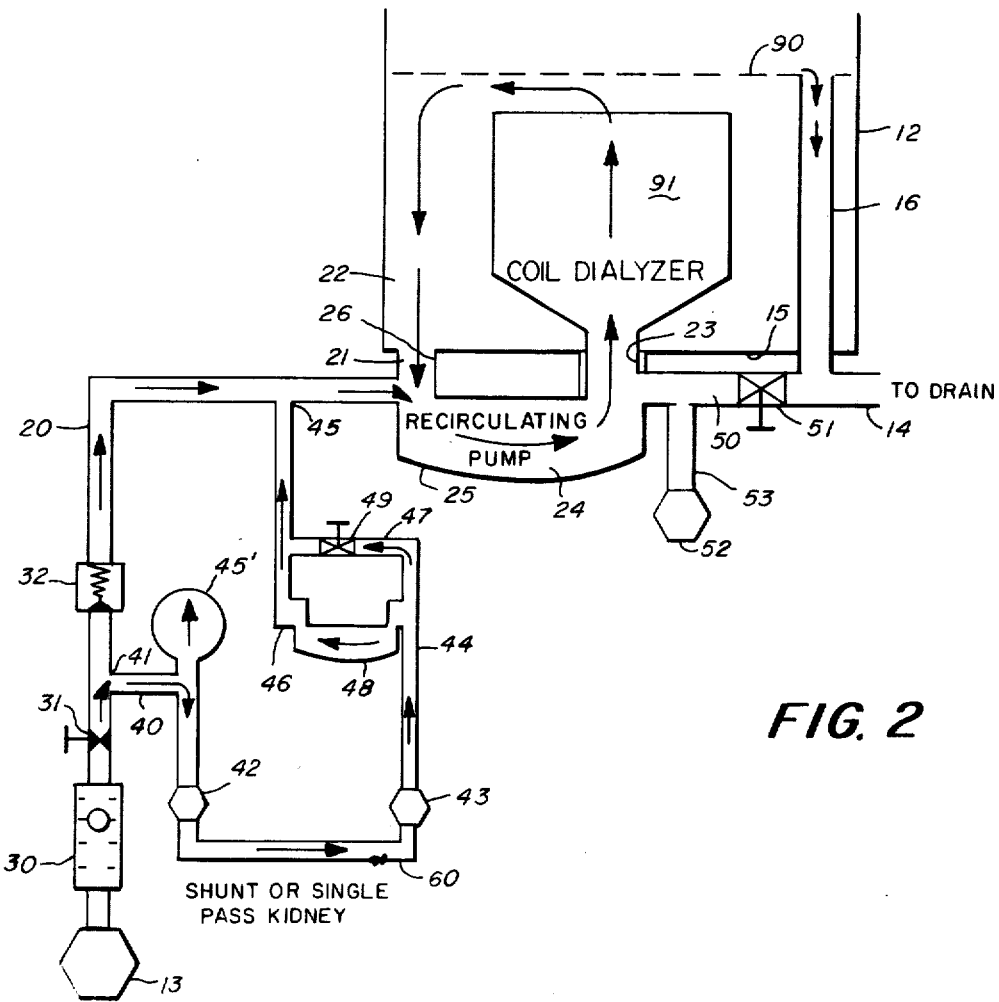
FIG. 2 is a semidiagrammatic drawing of the dialysate flow path system therein when used in a single pass-recirculating mode.

In the recirculating mode of operation shown in FIG. 2, a shunt pipe 50 is connected to self-sealing quick disconnects 42 and 43 thus providing a conduit therebetween. A single pass-recirculating dialyzer such as a coil dialyzer 91 is inserted in the opening 23 at the center of the canister. Flow of the dialysate from the central dialysate delivery system is as described above with regard to the single pass flow. However, the negative pressure pump is not in operation and the dialysate pressure regulating valve 49 is completely open. Thus dialysate flows into the recirculating system through pump 24 and fills the clear canister. When the level of fluid in the clear canister is sufficient to prevent air being drawn into the recirculating pump, the pump 24 is turned on. The dialysate content of the canister as for example 8 liters, is preset to a prescribed level such as indicated by the horizontal dotted line 90 in FIG. 2 with the overflow 16 limiting the level. The excess spent dialysate overflows and is passed out of the drain. In this mode of operation, fluid flow is indicated by the arrows shown with an acceptable low level of waste products in the dialysate maintained in the recirculating volume by the constant addition of fresh fluid.

The unit 10 can have a base housing dimension with a length of 14 inches, a width of 14 inches and a 7 inch height with the canister having a diameter of 12 inches and a height of 10 inches. Thus a highly compact unit is provided. All necessary controls for dialysate flow are accessible from the front panel of the unit as shown in FIG. 1. Switch 81 activates the recirculating pump 24 which is used only in the single pass-recirculating mode of operation. Switch 80 is an on-off switch for the negative pressure pump used only in conjunction with single pass operation. The quick disconnects 42 and 43 are readily accessible from the front of the machine for connection of the shunt line 60 or a single pass kidney 61. Similarly the flow meter and pressure gauge can be read through the indicators shown and they are controlled by control handles 82 and 83 for the flow valve 31 and valve 49. Conventional connections are made within the machine to provide for suitable wiring to the negative pressure pump 49 and recirculating pump 24 along with pump indicator lights 84 and 85. The electrical circuit is preferably such that the electrical components of the machine can be activated through conventional line current such as 120 volt 60 cycle current.

Either single pass or single pass-recirculating modes of operation allow use of 200 liters in a 6 hour period for the dialysate flow through the machine during a normal treatment period for a patient. In the single pass-recirculating mode of operation with the tank 12 holding an 8 liter volume of dialysate, in excess of 15 liters per minute can be recirculated with about 500 cc per minute of fresh dialysate added permitting a high dialysis flow rate through the system. Flow rates can be from 100 cc to 1 liter per minute if desired. No control over dialysate pressure is maintained since the system is open to the atmosphere. In single pass mode of operation using a parallel flow dialyzer, a similar flow rate can be maintained which is preferably about 500 cc per minute. The tank again holds 8 liters mainly to allow visual inspection. In single pass operation, the dialysate once past the kidney dialyzer can be drained through the drain valve 50 directly if no visual inspection is necessary. Control over pressure is accomplished by use of the negative pressure pump and the system is closed to the atmosphere up to the point of the negative pressure pump.

Cleaning of the apparatus can be accomplished in a number of ways. Generally, the quick disconnect 13 can be used to attach a cleaning solution which is then passed through the machine first in one mode then a second mode of operation using a shunt passageway 60. It should be noted that since all the conduiting in the system is used in both modes of operation, drying out of tubing and residual deposits of waste materials do not occur within the conduits.

While specific embodiments of the present invention have been shown and described, it will be obvious that many modifications are possible. For example, the particular materials of the conduiting, canister and the like can vary. The particular disconnects used as well as meters and pumps can be varied as known in the art. In all embodiments, single pass-recirculating mode of operation can be carried out by attachment of a recirculating dialyzer in the canister and a shunt conduit between quick disconnects 42 and 43 while single pass mode of operation can be accomplished by connection of a parallel flow dialyzer in the liquid circuit between quick disconnects 42 and 43. Although the pump 48 and valve 49 are preferably in separate conduits, other pumps can be used with series connected adjusting means. However, the preferred two conduit arrangement is preferred.

What is claimed is:

1. A dialysis apparatus for selective use with single pass or single pass-recirculating artificial kidney dialyzers to provide for dialysate flow, said apparatus comprising, a housing, a dialysate canister open to the atmosphere and carrying a dialysate overflow means for limiting a level of dialysate in said canister, a dialysate flow conduit having a first inlet for connection to a source of fresh dialysate and an outlet opening for passing dialysate to said canister, a mounting opening in said canister for detachably mechanically mounting an artificial kidney dialyzer therein, recirculating pump means having a conduit interconnecting one portion of said canister with said mounting opening for permitting dialysate recirculation therethrough, a first shunt dialysate conduit connected to said flow conduit at a first point intermediate said canister opening and said first inlet, said shunt dialysate conduit terminating at a first shunt connector, a second shunt connector spaced from said first shunt connector, a second shunt dialysis conduit leading from said second shunt connector to a second point for passing dialysate to said canister, said second shunt dialysate conduit having a negative pressure pump and means for adjusting the value of negative pressure produced by said pump.

2. A dialysis apparatus in accordance with claim 1 and further comprising a pressure relief valve means mounted in said dialysate flow conduit intermediate said first point and said canister for permitting through flow of dialysate from said first inlet upon buildup of pressure in said dialysate flow conduit above a predetermined value, said second point being located in said dialysate flow conduit, and said second shunt dialysate conduit having first and second branches intermediate ends thereof with one branch carrying a negative pressure pump and the second branch carrying said means for adjusting the value of negative pressure.

3. A dialysis apparatus in accordance with claim 2 and further comprising a flow meter and flow adjusting valve in said first conduit positioned between said first point and said first inlet.

4. A dialysis apparatus in accordance with claim 2 and further comprising said first and second shunt connectors being self-sealing, quick release, conduit connectors.

5. A dialysis apparatus in accordance with claim 2 and further comprising said dialysate canister being formed of a see-through material.

6. A dialysis apparatus in accordance with claim 2 and further comprising a shunt tube interconnecting said first and second shunt connectors, and a single pass recirculating artificial kidney dialyzer mounted in said canister mounting opening.

7. A dialysis apparatus in accordance with claim 2 and further comprising a single pass kidney dialyzer interconnected between said first and second shunt connectors to allow passage of dialysate therethrough.

8. A dialysis apparatus in accordance with claim 2 and further comprising, said overflow means being mounted in said canister for predetermining a level of dialysate therein and comprising an upwardly extending pipe connected to a drain.

9. A dialysis apparatus in accordance with claim 2 and further comprising, said overflow means mounted in said canister for predetermining a level of dialysate therein and comprising an upwardly extending pipe connected to a drain, said dialysate canister being formed of a see-through material, said first and second shunt connectors being self-sealing, quick release, conduit connectors, and a flow meter and a flow adjusting valve positioned in said first conduit between said first point and said first inlet.

10. A dialysis apparatus in accordance with claim 9 and further comprising a drain conduit having a first portion thereof interconnected with an outlet of said recirculating pump means, said drain conduit carrying a drain valve, a drain connector interconnected with said drain conduit intermediate said recirculating pump and said drain valve.

11. A dialysis apparatus in accordance with claim 2 and further comprising means for permitting selective actuation of said recirculating pump means and said negative pressure pump.

12. A dialysis apparatus for selective use with single pass or single pass-recirculating artificial kidney dialyzers to provide for dialysate flow, said apparatus comprising, a housing, a dialysate canister open to the atmosphere and carrying a dialysate overflow means for limiting a level of dialysate in said canister, a dialysate flow conduit having a first inlet for connection to a source of fresh dialysate and an outlet opening for passing dialysate to said canister, a mounting opening in said canister for detachably mechanically mounting an artificial kidney dialyzer therein, recirculating pump means having a conduit interconnecting one portion of said canister with a kidney dialyzer for permitting dialysate recirculation therethrough whereby said pump means can pump a minor amount of fresh dialysate from said outlet opening and a major amount of dialysate directly from said canister, a first shunt dialysate conduit connected to said flow conduit at a first point intermediate said canister opening and said first inlet, said shunt dialysate conduit terminating at a first shunt connector, a second shunt connector spaced from the first shunt connector, a second shunt dialysate conduit leading from said second shunt connector to a drain with said second shunt dialysate conduit having a negative pressure pump and means for adjusting the value of negative pressure produced by said pump.

13. A dialysis apparatus in accordance with claim 12 and further comprising said canister having a see-through construction to enable detection of blood leaks, and said second shunt dialysate conduit leading from said second shunt connector being interconnected with said canister before said drain.

14. A dialysis apparatus in accordance with claim 1 and further comprising said dialysate canister being formed of a see-through material.

15. A dialysis apparatus in accordance with claim 14 and further comprising said second point permitting dialysate flow to said recirculating pump means.

* * * * *